(12) United States Patent
Sun et al.

(10) Patent No.: US 9,422,300 B2
(45) Date of Patent: Aug. 23, 2016

(54) BISULFATE OF JANUS KINASE (JAK) INHIBITOR AND PREPARATION METHOD THEREFOR

(71) Applicant: Jiangsu Hengrui Medicine Co., Ltd., Lianyungang, Jiangsu (CN)

(72) Inventors: Piaoyang Sun, Jiangsu (CN); Guaili Wu, Jiangsu (CN); Xiaohui Gao, Jiangsu (CN); Lingjia Shen, Jiangsu (CN)

(73) Assignee: Jiangsu Hengrui Medicine Co., Ltd., Lianyungang, Jiangsu (CN)

( * ) Notice: Subject to any disclaimer, the term of this patent is extended or adjusted under 35 U.S.C. 154(b) by 0 days.

(21) Appl. No.: 14/895,117

(22) PCT Filed: May 5, 2014

(86) PCT No.: PCT/CN2014/076794
§ 371 (c)(1),
(2) Date: Dec. 1, 2015

(87) PCT Pub. No.: WO2014/194741
PCT Pub. Date: Dec. 11, 2014

(65) Prior Publication Data
US 2016/0102098 A1    Apr. 14, 2016

(30) Foreign Application Priority Data
Jun. 7, 2013 (CN) .......................... 2013 1 0227683

(51) Int. Cl.
*C07D 487/04*    (2006.01)
(52) U.S. Cl.
CPC .................... *C07D 487/04* (2013.01)
(58) Field of Classification Search
CPC ..................................................... C07D 487/04
USPC ....................... 514/265.1; 544/280
See application file for complete search history.

(56) References Cited

U.S. PATENT DOCUMENTS 7,192,963 B2    3/2007    Blumenkopf et al.

FOREIGN PATENT DOCUMENTS

| CN | 1439010 A | 8/2003 | | |
| CN | 1798559 A | 7/2006 | | |
| CN | WO 2013091539 A1 * | 6/2013 | ............ | A61K 45/06 |
| WO | 2012171863 A1 | 12/2012 | | |
| WO | 2013091539 A1 | 6/2013 | | |

OTHER PUBLICATIONS

International Search Report issued Aug. 4, 2014 in International Application No. PCT/CN2014/076794.

* cited by examiner

*Primary Examiner* — Kahsay Habte
(74) *Attorney, Agent, or Firm* — Panitch Schwarze Belisario & Nadel LLP

(57) ABSTRACT

The present invention relates to a bisulfate of a Janus kinase (JAK) inhibitor and a preparation method therefor. More specifically, the present invention relates to a (3aR,5s,6aS)—N-(3-methoxyl-1,2,4-thiadiazole-5-group)-5-(methyl(7H-pyrrolo[2,3-d]pyrimidine-4-group)amino)hexahydrocyclopenta[c]pyrrole-2(1H)-formamide bisulfate shown in the formula (I), a preparation method therefor, and an application thereof. The bisulfate shown in the formula (I) can be well suitable as a Janus kinase (JAK) inhibitor in clinical work for treating rheumatism or rheumatoid arthritis.

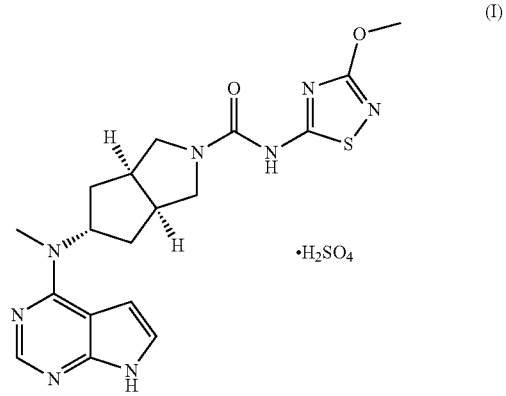

9 Claims, No Drawings

BISULFATE OF JANUS KINASE (JAK) INHIBITOR AND PREPARATION METHOD THEREFOR

CROSS-REFERENCE TO RELATED APPLICATION

This application is a Section 371 of International Application No. PCT/CN2014/076794, filed May 5, 2014, which was published in the Chinese language on Dec. 11, 2014 under International Publication No. WO 2014/194741 A1, and the disclosure of which is herein incorporated by reference.

FIELD OF THE INVENTION

The present invention relates to a bisulfate of a Janus kinase (JAK) inhibitor and a preparation method thereof. More specifically, the present invention relates to (3aR,5s,6aS)—N-(3-methoxyl-1,2,4-thiadiazol-5-yl)-5-(methyl(7H-pyrrolo[2,3-c]pyrimidin-4-yl)amino)hexahydrocyclopenta[c]pyrrole-2 (1H)-carboxamide bisulfate and a preparation method thereof.

BACKGROUND OF THE INVENTION

Arthritis is the most common chronic disease in the world, and there are many different reasons leading to, or causing arthritis, and joint injuries. Currently, the main drugs for the treatment of rheumatoid arthritis include adalimumab (Humira) of America Abbott Laboratories, etanercept (Enbrel) jointly developed by Pfizer and Amgen, and infliximab (Remicade) of Janssen Pharmaceutical Company. These, drugs are currently the best-selling drugs in the pharmaceutical market, but it is worth noting that these best-selling drugs are only injectable drugs. Although MTX (methotrexate), which is commonly administered orally, has pronounced efficacy, its toxicity is also significantly higher.

Studies, have shown that signaling pathway disorders of multiple cytokines play an important role in the pathophysiological process of rheumatoid arthritis (RA). The inflammatory cascade mediated by a series of uncontrolled cytokines leads to RA-related multiple cells, including T cells, B cells, monocytes, macrophages and osteoclasts in the long-term activated state, thereby causing persistent inflammation and joint structural damage. The Janus kinase (JAK) signaling pathway can regulate the proinflammatory activity of RA-related cells, wherein JAK is a hub protein in signal transduction of the inflammatory cytokine network, and the level of JAK is significantly increased in synovial tissues of RA joints. At present, tofacitinib (CP-690550) developed by Pfizer is a JAK1 inhibitor. The results of a phase III clinical trial showed that the efficacy of Pfizer's tofacitinib is significantly better than methotrexate. In this trial, the researchers randomly assigned patients, and one group of patients was administered 5 mg/10 mg of tofacitinib as a single drug, and the other group of patients were administered 5 mg/10 mg of methotrexate. The results showed that the efficacy of tofacitinib in reducing the progression of internal structural damage to human was slightly better than methotrexate in the period of six months, and that it could effectively improve various symptoms of rheumatoid arthritis patients.

We proceed from the idea of developing JAK kinase inhibitors following the global trend of drugs in the same category. Based on the structure of tofacitinib, we developed a series of drugs having in vitro and in vivo activities, and high absorption, and successfully obtained a compound of formula (IV) as a JAK kinase inhibitor. With regard to the compound of formula (IV), its information was completely described in PCT patent application No. PCT/CN2012/086922 filed jointly by the applicant together with other applicant, the content of which is herein incorporated by reference in its entirety.

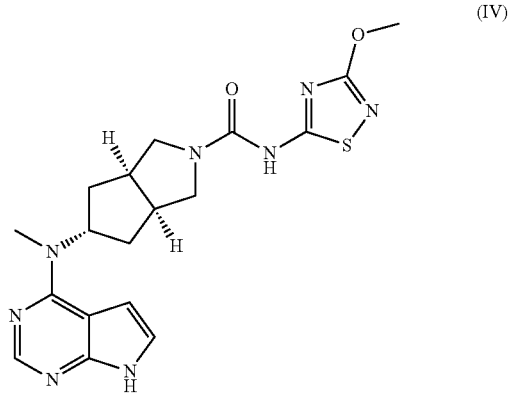

(IV)

Considering the lower solubility of the compound of formula (IV), we studied its salt-forms for improved solubility and bioavailability. The researched salts included salts of citric acid, hydrochloric acid and sulfuric acid. Based on the solubility data and pharmacokinetic results from animal experiments of the resulting salts, we surprisingly found that a compound of formula (I) was desirable to become a preferred JAK kinase inhibitor, which has a significant importance to the research and development in the treatment of rheumatism and rheumatoid arthritis.

DESCRIPTION OF THE INVENTION

The invention provides a JAK kinase inhibitor salt having better water-solubility and improved pharmacokinetic activity. More specifically, the invention provides (3aR,5s,6aS)—N-(3-methoxyl-1,2,4-thiadiazol-5-yl)-5-(methyl(7H-pyrrolo[2,3-d]pyrimidin-4-yl)amino)hexahydrocyclopenta[c]pyrrole-2(1H)-carboxamide bisulfate of formula (I) and a preparation method thereof.

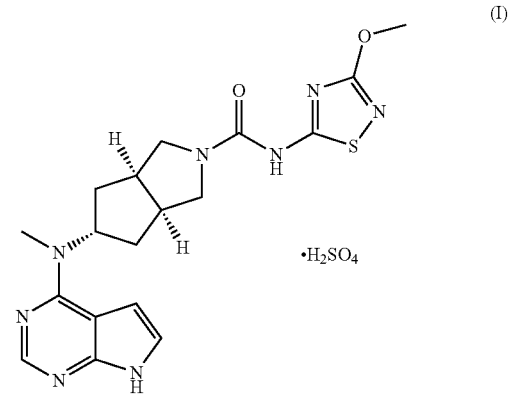

(I)

The stoichiometric ratio of (3aR,5s,6aS)—N-(3-methoxyl-1,2,4-thiadiazol-5-yl)-5-(methyl(7H-pyrrolo[2,3-a]pyrimidin-4-yl)amino)hexahydrocyclopenta[c]pyrrole-2(1H)-carboxamide to sulfuric acid is 1:1.

In another aspect, the invention provides a preparation method of (3aR,5s,6aS)—N-(3-methoxyl-1,2,4-thiadiazol-5-yl)-5-(methyl(7H-pyrrolo[2,3-d]pyrimidin-4-yl)amino)hexahydrocyclopenta[c]pyrrole-2(1H)-carboxamide bisulfate, comprising a step of a salt-forming reaction of a compound of formula (IV) with sulfuric acid.

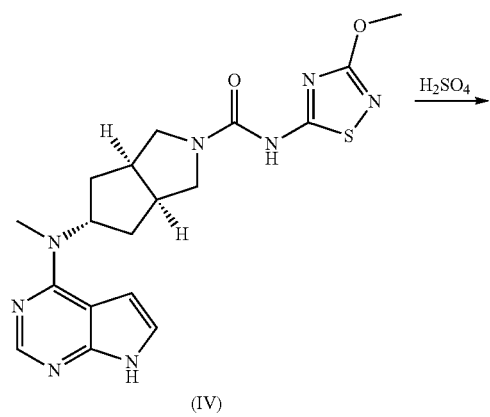

The above reaction can be carried out in a solvent, wherein the reaction solvent is a mixed solvent of haloalkanes and alcohols having less than or equal to 3 carbon atoms, preferably a mixed solvent of dichloromethane and methanol.

The temperature of the above reaction is preferably 10-30° C., and the reaction time is preferably 0.5-4 hours.

In another aspect, the invention provides a pharmaceutical composition comprising (3aR,5s,6aS)—N-(3-methoxyl-1,2,4-thiadiazol-5-yl)-5-(methyl(7H-pyrrolo[2,3-d]pyrimidin-4-yl)amino)hexahydrocyclopenta[c]pyrrole-2(1H)-carboxamide bisulfate of formula (I) and a pharmaceutically acceptable carrier.

In another aspect, the invention relates to use of (3aR,5s,6aS)—N-(3-methoxyl-1,2,4-thiadiazol-5-yl)-5-(methyl(7H-pyrrolo[2,3-d]pyrimidin-4-yl)amino)hexahydrocyclopenta[c]pyrrole-2(1H)-carboxamide bisulfate of formula (I) or a pharmaceutical composition comprising the same in the preparation of a medicament for the treatment of rheumatism and rheumatoid arthritis.

The bisulfite of formula (I) prepared in accordance with the method of the invention does not contain residual solvent, or only contains low amounts of residual solvent, and complies with the limit requirement of residual solvent of the relevant pharmaceutical products specified in the Chinese Pharmacopoeia. Thus, the bisulfate of formula (I) according to the invention can be well suitable as a pharmaceutical active ingredient.

PREFERRED EMBODIMENTS

The following examples serve to illustrate the invention in detail, and describe the technical solutions of the present invention. It should be understood that the following examples do not limit the spirit and the scope of the present invention.

Example 1

Preparation of the Compound of Formula (IV) (Described in PCT/CN2012/086922)

The compound of formula (IV) can be prepared in accordance with the following route:

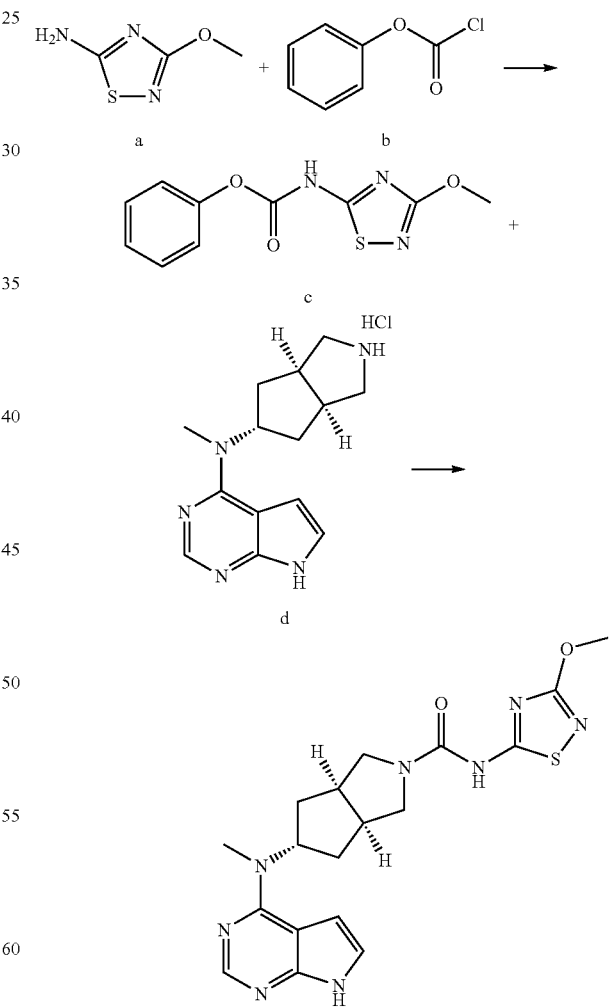

wherein the preparation of compound d is provided as follows:

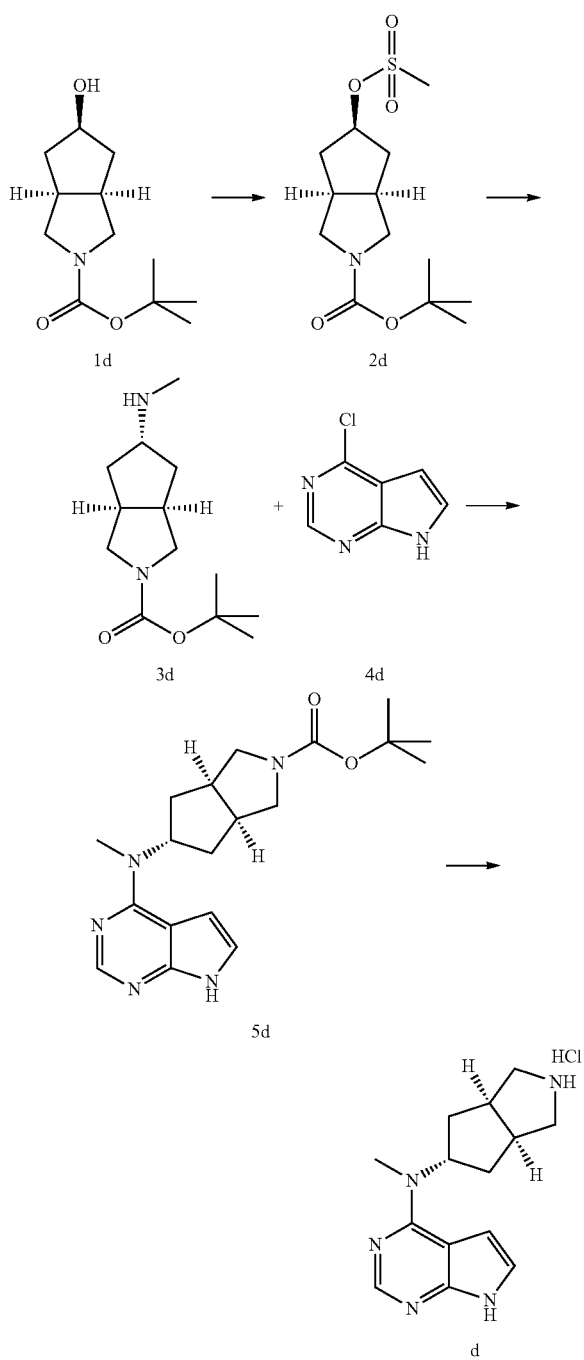

Specifically, the preparation of the compound of formula (IV) comprises the following two parts:

Part I

Preparation of Compound d

Step 1

(3aR,5r,6aS)-tert-butyl 5-((methylsulfonyl)oxy) hexahydrocyclopenta[c]pyrrole-2(1H)-carboxylate (3aR,5r,6aS)-tert-butyl 5-hydroxyhexahydrocyclopenta [c]pyrrole-2(1H)-carboxylate 1d (9 g, 40 mmol) was dis- solved in 150 mL of dichloromethane, followed by addition of methylsulfonyl chloride (4.70 mL, 60 mmol) and triethylamine (11.20 mL, 80 mmol) at 0° C. After reacting for 2 hours at room temperature, 200 mL of saturated sodium bicarbonate solution were added to the reaction mixture. The aqueous phase and organic phase were separated. The organic phase was washed with saturated sodium chloride solution (200 mL), dried over anhydrous magnesium sulfate, and filtered. The filtrate was concentrated under reduced pressure to obtain the title product (3aR,5r,6aS)-tert-butyl 5-((methylsulfonyl)oxy)hexahydrocyclopenta[c]pyrrole-2(1H)-carboxylate 2d (12.00 g, yield 98.4%) as a yellow liquid.

Step 2

(3aR,5s,6aS)-tert-butyl 5-(methylamino)hexahydro-cyclopenta[c]pyrrole-2(1H)-carboxylate (3aR,5r,6aS)-tert-butyl 5-((methylsulfonyl)oxy)hexahydrocyclopenta[c]pyrrole-2(1H)-carboxylate 2d (60 mg, 0.2 mmol) was dissolved in 10 mL of methanol, followed by addition of 5 mL of methylamine. After reacting for 16 hours at 40° C., the reaction mixture was concentrated under reduced pressure to obtain the crude title product (3aR,5s,6aS)-tert-butyl 5-(methylamino)hexahydrocyclopenta[c] pyrrole-2(1H)-carboxylate 3d (60 mg, brown oil), which was used directly in the next step without further purification.

MS m/z (ESI): 241.5 [M+1].

Step 3

(3aR,5s,6aS)-tert-butyl 5-(methyl(7H-pyrrolo[2,3-d] pyrimidin-4-yl)amino)hexahydrocyclopenta[c]pyrrole-2(1H)-carboxylate (3aR,5s,6aS)-tert-butyl 5-(methylamino)hexahydrocyclopenta[c]pyrrole-2(1H)-carboxylate 3d (200 mg, 0.8 mmol) and 4-chloro-7H-pyrrolo[2,3-d]pyrimidine 4d (127 mg, 0.8 mmol) were dissolved in 5 mL of n-butanol, followed by addition of triethylamine (168 mg, 1.6 mmol). After reacting for 48 hours at 100° C., the reaction mixture was concentrated under reduced pressure, followed by addition of 10 mL of $H_2O$ and 10 mL of ethyl acetate. The aqueous phase and organic phase were separated. The organic phases were combined, dried over anhydrous sodium sulfate, and filtered. The filtrate was concentrated under reduced pressure, and the resulting residue was purified by HPLC to obtain the title product (3aR,5s,6aS)-tert-butyl 5-(methyl(7H-pyrrolo[2,3-d]pyrimidin-4-yl)amino)hexahydrocyclopenta[c]pyrrole-2 (1H)-carboxylate 5d (5 mg, yield 5.0%) as a white solid.

MS m/z (ESI): 358.5[M+1]

$^1$H NMR (400 MHz, $CDCl_3$): δ 10.07 (s, 1H), 8.31 (s, 1H), 7.50 (s, 1H), 6.55 (s, 1H), 5.58-5.54 (m, 1H), 3.65-3.62 (m, 2H), 3.27-3.23 (m, 5H), 2.86-2.81 (m, 2H), 2.06-2.02 (m, 2H), 1.93-1.91 (m, 2H), 1.49 (s, 6H).

Step 4

N-Methyl-N-((3aR,5s,6aS)-octahydrocyclopenta[c] pyrrol-5-yl)-7H-pyrrolo[2,3-d]pyrimidin-4-amine hydrochloride (3aR,5s,6aS)-tert-butyl 5-(methyl(7H-pyrrole[2,3-d]pyrimidin-4-yl)amino)hexahydrocyclopenta[c]pyrrole-2(1H)- carboxylate 5d (1.5 g, 4.2 mmol) was dissolved in 20 mL of a solution of 1M hydrogen chloride in methanol. After reacting for 16 hours, the reaction mixture was concentrated under reduced pressure to obtain the crude title product N-Methyl-N-((3aR,5s,6aS)-octahydrocyclopenta[c]pyrrol-5-yl)-7H-pyrrolo[2,3-d]pyrimidin-4-amine hydrochloride d (1.5 g, brown solid).

MS m/z (ESI): 258.1 [M+1].

Part II

Preparation of the Compound of Formula (IV)

Step 1

Phenyl(3-methoxy-1,2,4-thiadiazol-5-yl)carbamate

3-Methoxy-1,2,4-thiadiazol-5-amine a (500 mg, 3.82 mmol) and phenyl carbonochloridate b (600 mg, 3.82 mmol) were dissolved in 20 mL of dichloromethane, followed by addition of triethylamine (0.8 mL, 5.73 mmol). After reacting for 16 hours, 30 mL of $H_2O$ were added into the reaction mixture to dilute the solution. The aqueous phase and organic phase were separated, the aqueous phase was extracted with dichloromethane (20 mL×2), and the organic phases were combined, dried over anhydrous sodium sulfate, and filtered. The filtrate was concentrated under reduced pressure, and the resulting residue was purified by silica gel column chromatography with elution system A to obtain the title product phenyl(3-methoxy-1,2,4-thiadiazol-5-yl)carbamate c (200 mg, yield 20.8%) as a white solid.

MS m/z (ESI): 252.0 [M+1].

Step 2

(3aR,5s,6aS)—N-(3-Methoxy-1,2,4-thiadiazol-5-yl)-5-(methyl(7H-pyrrolo[2,3-d]pyrimidin-4-yl)amino) hexahydrocyclopenta[c]pyrrol-2(1H)-carboxamide N-Methyl-N43aR,5s,6aS)-octahydrocyclopenta[c]pyrrol-5-yl)-7H-pyrrolo[2,3-d]pyrimidin-4-amine hydrochloride d (120 mg, 0.47 mmol) was dissolved in 15 mL of tetrahydrofuran, followed by addition of phenyl(3-methoxy-1,2,4-thiadiazol-5-yl)carbamate c (117 mg, 0.47 mmol) and triethylamine (0.13 mL, 0.94 mmol). After reacting for 5 hours at 60° C., the reaction mixture was mixed with 30 mL of $H_2O$ and extracted with dichloromethane (50 mL×3). The organic phases were combined, washed with saturated sodium chloride solution (50 mL×2), dried over anhydrous sodium sulfate, and filtered. The filtrate was concentrated under reduced pressure, and the resulting residue was purified by silica gel column chromatography with elution system A to obtain the title product (3aR,5s,6aS)—N-(3-Methoxy-1,2,4-thiadiazol-5-yl)-5-(methyl(7H-pyrrolo[2,3-d]pyrimidin-4-yl)amino) hexahydrocyclopenta[c]pyrrol-2(1H)-carboxamide (IV) (50 mg, yield 25.9%) as a white solid.

MS m/z (ESI): 412.9 [M−1].

$^1$H NMR (400 MHz, DMSO-$d_6$): δ 11.60 (m, 2H), 8.08 (s, 1H), 7.06-7.05 (m, 1H), 6.53-6.51 (m, 1H), 5.48-5.44 (m, 1H), 3.90 (s, 3H), 3.69-3.65 (m, 2H), 3.37-3.32 (m, 2H), 3.16 (s, 3H), 2.90-2.88 (m, 2H), 2.02-1.99 (m, 2H), 1.80-1.77 (m, 2H).

Example 2

Preparation of (3aR,5s,6aS)—N-(3-methoxyl-1,2,4-thiadiazol-5-yl)-5-(methyl(7H-pyrrolo[2,3-d]pyrimidin-4-yl)amino)hexahydrocyclopenta[c]pyrrole-2(1H)-carboxamide bisulfate (the compound of formula (I))

(3aR,5s,6aS)—N-(3-Methoxy-1,2,4-thiadiazol-5-yl)-5-(methyl(7H-pyrrolo[2,3-d]pyrimidin-4-yl)amino)hexahydrocyclopenta[c]pyrrol-2(1H)-carboxamide (IV) (140 g, 0.34 mol), anhydrous methanol (350 g) and dichloromethane (2.0 kg) were added to a 10 L reaction flask under stirring. Sulfuric acid (34.8 g, 0.36 mol) was added slowly at room temperature, and the reaction solution became clear. After stirring for 30 minutes, the insoluble material was removed by filtration, the filtrate was concentrated under reduced pressure, and then dried to obtain the title product 135 g-168 g, yield: 80-90%.

MS m/z (ESI): 415.1651 [M+1].

$^1$H NMR (400 MHz, DMSO-$d_6$): δ 12.75 (s, 1H), 11.04 (s, 1H), 8.37 (s, 1H), 7.41-7.42 (t, 1H), 6.89 (s, 1H), 5.15-5.19 (m, 1H), 3.89 (s, 3H), 3.68-3.70 (m, 2H), 3.38-3.40 (m, 2H), 3.29 (s, 3H), 2.95 (s, 2H), 2.09-2.16 (m, 2H), 1.92-1.97 (m, 2H).

Example 3

Comparative solubility experiments of (3aR,5s,6aS)—N-(3-methoxyl-1,2,4-thiadiazol-5-yl)-5-(methyl(7H-pyrrolo[2,3-d]pyrimidin-4-yl)amino)hexahydrocyclopenta[c]pyrrole-2(1H)-carboxamide (the compound of formula (IV)) and its corresponding citrate, hydrochloride, sulfate, bisulfate in water and 0.1N HCl salts were carried out. The results showed that the solubility of the bisulfate salt was greatly increased, and was also much better than other salts. The detailed results are shown in Table 1.

TABLE 1

Comparative solubility experiments of the compound of (IV) and its salts

| Compound | Solvent | Solubility | Conclusion |
| --- | --- | --- | --- |
| Compound of formula (IV) | Water | 10000 ml/g | insoluble |
|  | 0.1N HCl | — | — |
| Citrate | Water | 10000 ml/g | insoluble |
|  | 0.1N HCl | 160 ml/g | slightly soluble |
| Hydrochloride | Water | 1500 ml/g | very slightly soluble |
|  | 0.1N HCl | 10000 ml/g | insoluble |
| Sulfate | Water | 10000 ml/g | insoluble |
|  | 0.1N HCl | 2500 ml/g | very slightly soluble |
| Bisulfate | Water | 70 ml/g | slightly soluble |
|  | 0.1N HCl | 50 ml/g | slightly soluble |

Example 4

The pharmacokinetic parameters of the compound of formula (IV) and its different salt forms were studied in rhesus monkeys, and the properties of the different forms of the compounds were evaluated in detail. Four rhesus monkeys were used as test animals, half male and half female. The rhesus monkeys were administered a single dose of 50 mg/kg. Multi-crossover design was adopted to administer different drugs to test animals, and the convalescence from each cycle was three days. Blood samples (0.5 mL) were taken from the femoral vein before administration (0 h), and at 0.25 h, 0.5 h, 1 h, 2 h, 4 h, 6 h, 8 h and 24 h after administration, stored in heparinized tubes, shaken well, and centrifuged for 10 minutes at 3500 rpm to separate blood plasma. The plasma samples were stored at low temperature, LC-MS/MS was used to measure drug concentration in plasma and liver, and pharmacokinetic parameters were analyzed by WinNonlin 5.3 software. The experimental results are shown as follows:

TABLE 2

Pharmacokinetic parameters of the compound of formula (IV), its citrate, and bisulfate

| | Dose mg/kg | Administration time day(s) | $t_{1/2}$ Hour | $AUC_{(0-t)}$ ng/ml * hour | MRT hour | Cmax ng/ml |
|---|---|---|---|---|---|---|
| Compound of formula (IV) | 50 | single dose | 6.3 ± 3.5 | 41111 ± 59593 | 8.8 ± 5.16 | 6176 ± 8838 |
| Citrate | 50 | | 6.3 ± 5.5 | 44357 ± 45012 | 10.0 ± 7.6 | 5627 ± 4201 |
| Bisulfate | 50 | | 5.3 ± 1.6 | 63007 ± 53558 | 6.3 ± 1.7 | 9940 ± 5325 |

CONCLUSIONS

The pharmacokinetic results in monkeys above showed that the in vivo exposure of the compound of formula (IV) is 41111 ng/ml*h, with a relatively large individual variation. The in vivo exposure of the citrate salt is similar to that of the base. The in vivo exposure of the bisulfate salt increased by 50% relative to that of the base, with a relatively small individual variation. It can be seen that the bisulfate salt had high in vivo exposure and a small individual variation, and is thus suitable for medicinal purposes.

What is claimed is:

1. (3aR,5s,6aS)—N-(3-methoxyl-1,2,4-thiadiazol-5-yl)-5-(methyl(7H-pyrrolo[2,3-d]pyrimidin-4-yl)amino)hexahydrocyclopenta[c]pyrrole-2(1H)-carboxamide bisulfate of formula (I)

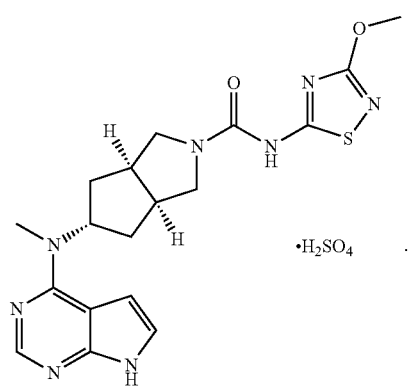

2. (3 aR,5s,6aS)—N-(3-methoxyl-1,2,4-thiadiazol-5-yl)-5-(methyl(7H-pyrrolo[2,3-d]pyrimidin-4-yl)amino)hexahydrocyclopenta[c]pyrrole-2(1H)-carboxamide bisulfate of formula (I) according to claim 1, wherein a stoichiometric ratio of a compound of formula (IV) to sulfuric acid is 1:1:

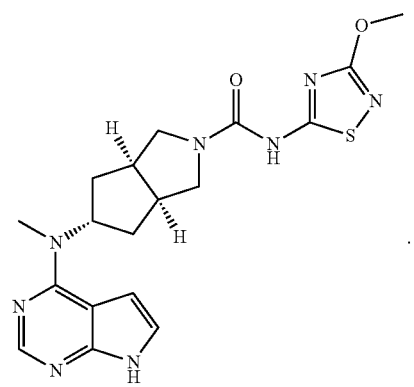

3. A preparation method, of (3aR,5s,6aS)—N-(3-methoxyl-1,2,4-thiadiazol-5-yl)-5-(methyl(7H-pyrrolo[2,3-d]pyrimidin-4-yl)amino)hexahydrocyclopenta[c]pyrrole-2(1H)-carboxamide bisulfate of formula (I) according to claim 1, comprising a step of reacting a compound of formula (IV) with sulfuric acid, thereby forming a salt of formula (I)

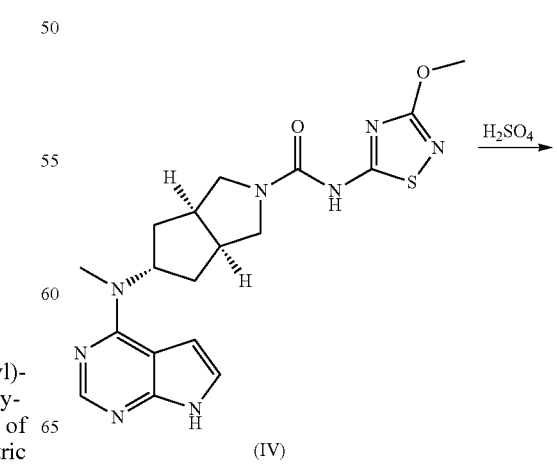

-continued

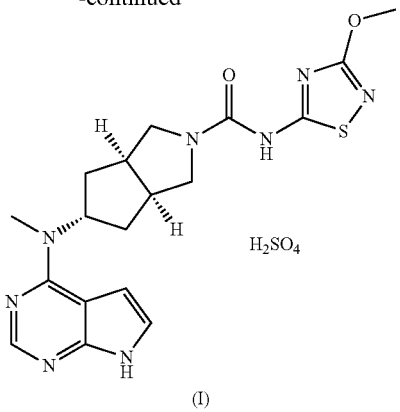

(I)

4. The preparation method according to claim 3, wherein the salt-forming reaction is carried out in a solvent, and the solvent is a mixed solvent of haloalkanes and alcohols having less than or equal to 3 carbon atoms.

5. The preparation method according to claim 4, wherein the reaction temperature of the salt-forming reaction is 10-30° C., and the reaction time is 0.5-4 hours.

6. A pharmaceutical composition comprising the (3aR,5s,6aS)—N-(3-methoxyl-1,2,4-thiadiazol-5-yl)-5-(methyl(7H-pyrrolo[2,3-d]pyrimidin-4-yl)amino)hexahydrocyclopenta[c]pyrrole-2(1H)-carboxamide bisulfate of formula (I) according to claim 1 and a pharmaceutically acceptable carrier.

7. The preparation method according to claim 4, wherein the solvent is a mixed solvent of dichloromethane and methanol.

8. A method of treating rheumatism or rheumatoid arthritis in a subject in need thereof, the method comprising administering to the subject (3aR,5s,6aS)—N-(3-methoxyl-1,2,4-thiadiazol-5-yl)-5-(methyl(7H-pyrrolo[2,3-d]pyrimidin-4-yl)amino)hexahydrocyclopenta[c]pyrrole-2(1H)-carboxamide bisulfate of formula (I) according to claim 1.

9. A method of treating rheumatism or rheumatoid arthritis in a subject in need thereof, the method comprising administering to the subject the pharmaceutical composition according to claim 6.

* * * * *